United States Patent [19]

Miyake et al.

[11] Patent Number: 5,003,638
[45] Date of Patent: Apr. 2, 1991

[54] STERILIZED GLOVE

[75] Inventors: Teruyoshi Miyake; Tatsuo Yamamoto, both of Tokyo, Japan

[73] Assignees: Chyugoku Paalu Distributing Corporation; Shinanen New Ceramic Corporation; Shinagawa Fuel Co., Ltd., all of Tokyo, Japan

[21] Appl. No.: 496,671

[22] Filed: Mar. 21, 1990

[30] Foreign Application Priority Data

Dec. 27, 1989 [JP]  Japan .................................. 1-338949

[51] Int. Cl.⁵ ............................................. A41D 13/10
[52] U.S. Cl. ........................................... 2/167; 2/168; 2/161 R
[58] Field of Search ............... 2/159, 161 R, 167, 168, 2/169

[56] References Cited

U.S. PATENT DOCUMENTS

| 4,525,410 | 6/1985 | Hagiwara et al. | 424/411 X |
| 4,775,585 | 10/1988 | Hagiwara et al. | 428/323 |
| 4,906,464 | 3/1990 | Yamamoto et al. | 424/79 X |
| 4,938,955 | 7/1990 | Niira et al. | 424/79 |
| 4,938,958 | 7/1990 | Niira et al. | 424/79 |

FOREIGN PATENT DOCUMENTS

| 240994 | 12/1960 | Australia | 2/167 |
| 300814 | 1/1989 | European Pat. Off. | 2/168 |
| 2015308 | 1/1987 | Japan | 2/168 |

Primary Examiner—Werner H. Schroeder
Assistant Examiner—Sara M. Current

[57] ABSTRACT

A sterilized glove comprises a glove body and an organic polymer film layer containing an antibacterial zeolite and formed on the entirety of at least one surface of the glove body in an upheaval shape.

6 Claims, 2 Drawing Sheets

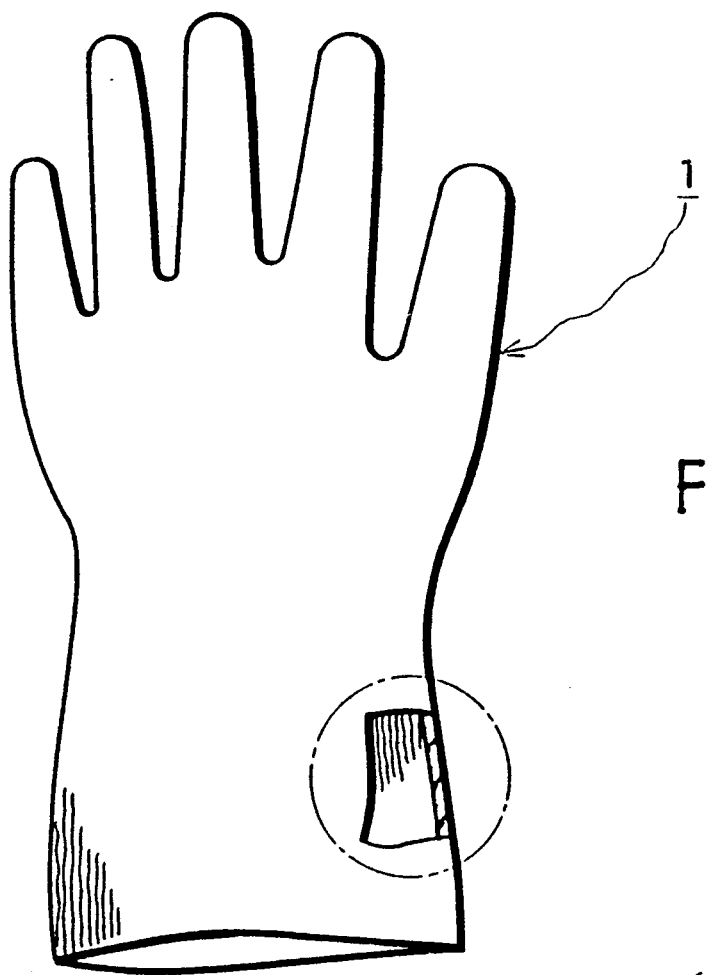
FIG. IA
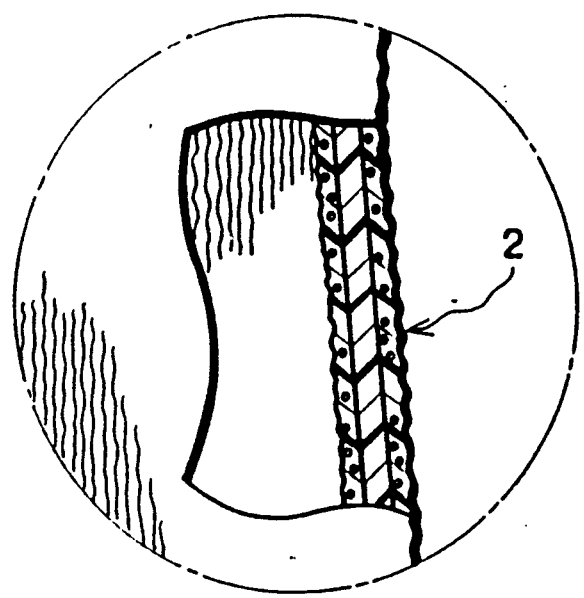
FIG. IB

STERILIZED GLOVE

BACKGROUND OF THE INVENTION

The present invention relates to a glove, especially to a glove having an organic polymer film layer containing an antibacterial zeolite and formed on the entirety of at least one surface of the glove body so as to be suitable in handling foods or the like.

All kinds of popular operation gloves such as working gloves for handling foods, medical gloves, kitchen gloves which prevent chapped fingers, are usually made by a secondary processing of extruded film or sheet formed from thermoplastic resin, or made by covering a surface of a woven fabric with resin layers.

The surfaces of said gloves have not been protected against pollutions at a distribution stage or at a storage stage. Moreover, due to their bad ventilation in use, the gloves do not allow for the evaporation of sweat, but do allow for the breeding of microbes on their inner surfaces. That ended up with giving off a bad smell.

As a solution to said bad influence on the microbe, there has been proposed a glove having an antibacterial ion containing zeolite (so-called antibacterial zeolite) kneaded therein which is highly safe for human bodies (refer to Unexamined Published Japanese Utility Model Application Serial No. 62-201607).

Unlike conventionally used germicides or bactericide, an antibacterial zeolite is an excellent bactericide in that its antibacterial material will not be dissolved and come out or be vaporized, so that it hardly alters the taste of food or is hardly virulent. Further, the sterilized effect of the antibacterial material will last longer.

In processing this antibacterial zeolite into a glove, however, if it is simply kneaded and is filmed in a resin such as polyethylene, a small amount of the antibacterial zeolite exists merely in a part of the surface of the glove to present the sterilization effect, but most of it is in the resin and does not contribute to the sterilization effect at all.

SUMMARY OF THE INVENTION

Accordingly, it is an object of this invention to provide a sterilized glove which can present a sufficient antibacterial property with a relatively small amount of an antibacterial zeolite and can be fabricated using substantially the same method for producing conventional gloves.

To achieve this object, there is provided a sterilized glove comprising a glove body and an organic polymer film layer containing an antibacterial zeolite and formed on the entirety of at least one surface of the glove body in an upheaval shape.

BRIEF DESCRIPTION OF THE DRAWINGS

FIG. 1A is a perspective view and a partial enlarged illustrating a sterilized glove embodying this invention;

FIG. 1B is a partial enlarged view of a section of the glove shown in FIG. 1A.

DESCRIPTION OF THE PREFERRED EMBODIMENT

Figure 2:
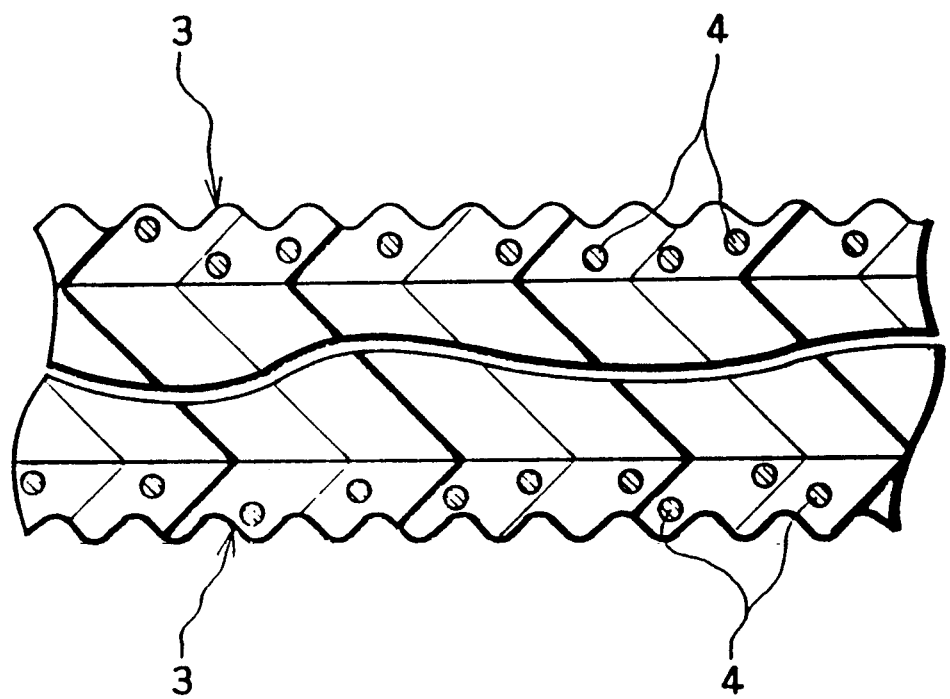
FIG. 2 is an enlarged cross sectional view of the glove material used in this invention.

A sterilized glove according to this invention can be provided by forming an organic polymer film layer containing about 3 μm or more of an antibacterial zeolite on the entire outer and inner surfaces of a glove body, and making the outer and inner surfaces upheaval.

An "antibacterial zeolite" used in this invention has a part or all of exchangeable ions in a zeolite exchanged with an antibacterial ion. Such an antibacterial ion may be a silver ion, copper ion, or zinc ion, for example. Alternately, the antibacterial zeolite may be a zeolite having an ion exchanged with an ammonium ion in order to prevent discoloration of resin with time.

The zeolite can be a natural zeolite or a synthesized one. Zeolite in general is an aluminosilicate having a three dimensional skeleton structure, and is generally expressed by $XM_{2/n}O \cdot Al_2O_3 \cdot YS_{i2}O_2 \cdot ZH_2O$, where M is an exchangeable ion which is normally a univalent or bivalent metal ion, n is the valence of the (metal) ion, X and Y are a metal oxide and silica coefficient, and Z is the number of crystal water. Practical examples of the zeolite may include an A-type zeolite, X-type zeolite, Y-type zeolite, T-type zeolite, high silica zeolite, sodalite, mordenite, analcime, clinoptilolite, chabazite, and erionite, though not limited to those mentioned. The exemplified zeolites have the following ion-exchange capacities: 7 meq/g for the A-type zeolite, 6.4 meq/g for the X-type zeolite, 5 meq/g for the Y-type zeolite, 3.4 meq/g for the T-type zeolite, 11.5 meq/g for the sodalite, 2.6 meq/g for the mordenite, 5 meq/g for the analcime, 2.6 meq/g for the clinoptilolite, 5 meq/g for the chabazite, and 3.8 meq/g for the erionite. These ion-exchange capacities are sufficient for ensuring ion exchange with an antibacterial ion such as an ammonium ion or silver ion. The antibacterial ion may be a silver ion, copper ion, zinc ion, bismuth ion, tin ion or thallium ion; it is preferably the silver ion, copper ion or zinc ion.

In view of the antibacterial property, it is preferable that the zeolite should contain 0.1 to 15 % of an antibacterial ion. It is more preferable that the antibacterial zeolite should contain 0.1 to 15 % of the silver ion or 0.1 to 18 % of the copper ion or zinc ion. In consideration of effectively preventing the discoloration of a resin containing the zeolite, the proper amount of the ammonium ion contained in the zeolite is 0.5 to 5 %, preferably 0.5 to 2 %. In this specification, "%" means the weight % with 110° C. being the reference drying temperature.

The following will describe how to fabricate a antibacterial zeolite.

The antibacterial zeolite used in this invention can be provided by rendering a zeolite to contact a mixed solution containing a preadjusted antibacterial ion, such as a silver ion, copper ion or zinc ion, and an ammonium ion, to thereby exchange the exchangeable ion in the zeolite with the former ions. The contact is performed under a temperature of 10° to 70° C., preferably 40° to 60° C., for 3 to 24 hours, more preferably for 10 to 24 hours, using the batch operation or continuous operation (e.g., column operation). The mixed solution should have its pH controlled to be 3 to 10, and preferably 5 to 7, as such control can prevent precipitation of a silver oxide or the like into the surface or pores of the zeolite. Each ion in the mixed solution is normally supplied as a salt. For instance, the silver ion may be supplied using a silver nitrate, silver sulfate, silver perchlorate, silver acetate, diamine silver nitrate or diamine silver sulfate, the copper ion may be supplied using a copper nitrate (II), copper sulfate, copper perchlorate, copper acetate or potassium tetracyanocuprate, the zinc ion may be supplied using a zinc nitrate (II) or zinc sulfate, the bismuth ion may be supplied using a bismuth chloride or bismuth iodide, and the thallium ion may be supplied using a thallium perchlorate, thallium sulfate, thallium nitrate or thallium acetate.

The amount of the silver ion, etc. in the zeolite can be properly controlled by adjusting the density of each ion (salt) in the mixed solution. In a case where the antibacterial zeolite contains the ammonium ion and silver ion, for instance, this antibacterial zeolite will properly contain 0.5 to 5 % of the ammonium ion and 0.1 to 15 % of the silver ion by adjusting the ammonium ion density and the silver ion density in the mixed solution to be 0.2 M/1 to 2.5 M/1 and 0.002 M/1 to 0.45 M/1, respectively. In a case where the antibacterial zeolite further contains the copper ion and zinc ion, for instance, this antibacterial zeolite will properly contain 0.1 to 18 % of the copper ion and 0.1 to 18 % of the zinc ion by adjusting the copper ion density and the zinc ion density in the mixed solution to be 0.1 M/1 to 2.3 M/1 and 0.15 M/1 to 2.8 M/1, respectively.

The ion exchange may also be performed by using solutions containing the respective ions, instead of the aforementioned mixed solution, and causing the zeolite to properly contact the individual solutions. The ion density in each solution can be determined in conformity to the associated ion density in the mixed solution.

The zeolite having undergone the ion exchange is dried after it is sufficiently cleaned by water. To prevent the film contained in the antibacterial zeolite from the occurrence of pinholes, it is desirable that the zeolite having undergone the ion exchange should be dried at the molding temperature of the organic polymer film layer containing the antibacterial zeolite under a condition in which no water is evaporated from the zeolite. For instance, it is preferable that the drying is performed so that the remaining water in the zeolite becomes 4 % or below. Such drying may properly be performed at 105° to 400° C. under the normal pressure or 50° to 250° C. under a reduced pressure (about 1 to 30 Torr).

In order to provide a sterilized glove having a high antimicrobial activity, the antibacterial zeolite used in this invention should have an average particle diameter of 4 $\mu$m or below, preferably 0.3 to 2 $\mu$m. The organic polymer for the organic polymer film layer used for the present sterilized glove may be an ionomer resin, EEA resin, EVA resin, polyvinyl chloride, chlorinated polyethylene, fluoride resin, polyamide resin, thermoplastic polyurethane elastomer, polyether ether ketone resin, polysulfone, high density polyethylene, low density polyethylene, liner low density polyethylene, polycarbonate, butadiene resin, polypropylene, styren type special transparent resin, polyacrylate, reinforced polyethylene terephthalate, polystyrene, vinylidene chloride resin or electroconductive resin (e.g., Shostat, a product of SHOWA DENKO K.K.). In view of the processability and water-resistance, polyethylene such as the high density polyethylene, low density polyethylene or liner low density polyethylene is preferable.

The organic polymer film layer used in this invention will now be described.

The organic polymer film layer used in the present sterilized glove can be provided by molding (filming) a mixture attained by mixing the antibacterial zeolite and the organic high-molecular compound by the normal method.

The molding method may be casting molding, extrusion molding (for example, film blowing molding, T die molding, calendering molding, cutting method or the like) and stretching method. The casting molding, for example, comprises the steps of adding an antibacterial zeolite (and an additive such as a plasticizer in case of necessity) to a solution dissolving materials of resin flakes in water or in an organic solvent, spreading a mixture of the antibacterial zeolite and the solution over a supporting plate after filtering and defoaming to provide a thin film.

In order to ensure economically effective use of the antibacterial zeolite and keep sterilized properties, it is preferable that the organic polymer film layer used in this invention have a thickness of 3 $\mu$m or above, preferably 15 to 50 $\mu$m. Further, it is preferable to mix 1 to 400 mg, preferably 2 to 100 mg, of the antibacterial zeolite per 1 $m^2$ of the organic polymer film layer in order to stably keep the sterilized state.

Meanwhile the present sterilized glove may also take a laminated molding structure laminating the organic polymer film layer containing the antibacterial zeolite on a resin layer of a glove body. Further, conventional materials used for the resin layer of the glove body may be a polystyrene, ABS resin, AS resin, polyethylene, polypropylene, SBR resin, EVA resin, polyvinyl chloride, polymethylmethacrylate, polyamide resin, polycarbonate, polyethylene telephthalate, polymethylpentene, fluoride resin, polysulfone, oxibenzoyl polyester or polybutene.

This resin layer may be processed as a foaming member.

Moreover, a piqment or an inorganic substance may be added to the resin layer to provide a colorful glove in blue, pink, etc.

The thickness of the resin layer of the glove body used in this invention may vary depending on the use of the present sterilized glove and constituting materials; for example, it is set to be 30 to 1000 $\mu$m.

Known conventional methods such as the thermally melting pressure bonding method, coextrusion method, gluing method, extrusion method, hot melting method, dry laminate method and wet laminate method can all be applied as a method for laminating the film layer containing the antibacterial zeolite on the resin layer of the glove body in the present sterilized glove.

As the present sterilized glove has upheavals formed on its surfaces, the sterilization lasting force can be provided more effectively. In view of increasing the sterilization lasting force, the proper area of the upheavals is 120 % or more, preferably 150 % or more, of the area of the glove's surfaces when they are flat. Making the upheavals 1 to 3 mm high in the direction of the thickness of the glove causes the antibacterial zeolite to be more exposed and is most preferable when the glove is in use. Further, it is better that the upheavals may be formed uniformly over the surfaces of the glove; the upheavals may be formed in a geometric pattern of about 1 to 3 mm. The upheavals may be formed on the surfaces of the present sterilized glove by using a method for pressing a thermally melt, molded film onto an emboss roll or a mat roll with an upheaval pattern provided by putting a mirror-finished roll to corrosion process or mechanical process.

The film layer containing the antibacterial zeolite in the present sterilized glove may be formed on both the outer and the inner surface of the glove body in an upheaval shape. In this way, it is better to prevent a food and a chemical to be handled from incurring microbe pollution.

The present invention will be described in more detail below referring to specific examples.

Example of Adjusting Antibacterial Zeolite

In this invention two types of zeolites were used; A-type zeolite ($Na_2O \cdot Al_2O_3 \cdot 1.9SiO_2 \cdot XH_2O$: average particle size of 1.5 μm) and Y-type zeolite ($1.1Na_2O \cdot Al_2O_3 \cdot 4.0SiO_2 \cdot XH_xO$: average particle size of 0.7 μm) both available on the market. Four types of salts for individual ion exchanges were used: silver nitrate, copper nitrate, zinc nitrate and ammonium nitrate. Table 1 shows the types and densities of salts contained in an ion-exchange solution with respect to the types of zeolites used in adjusting each sample.

For each sample, water was added to 1 Kg of powder heated and dried at 110° C. to provide 1.3 l of slurry, then the slurry was stirred for deairing, and proper amounts of 0.5 N nitrate solution and water were added to the slurry to control its pH to be 5 to 7 to thereby provide 1.8 l of slurry in total. Then, 3 l of a solution of a predetermined salt having a predetermined density was added to the slurry for ion exchange and the resultant slurry had a total volume of 4.8 l. This slurry liquid was stirred to be in a uniform state for 10 to 48 hours while being kept at 40° to 60° C. After ion exchange, the zeolite phase was filtered and washed with water of a room temperature or warm water using excess silver ions, etc. in the zeolite phase until no more ion components could be detected. Then, data on the individual samples 1 to 4 heated and dried at 110° C. were acquired. The resultant data are as shown in Table 1.

FABRICATION EXAMPLE OF STERILIZED GLOVE

The antibacterial zeolite attained in the manner described in the previous section, "Example of Adjusting Antibacterial Zeolite," was dried for 5 hours under predetermined drying conditions (amount of remaining water being 3.8 % or less). A low density polyethylene (Nobatec F161, a product of MITSUBISHI CHEMICAL INDUSTRIES LTD.) was added to the dried antibacterial zeolite so that the amount of the antibacterial zeolite became 10 to 40 mg/m². The resultant antibacterial film layer 30 μm in thickness, together with layer made only of a low density polyethylene and a layer further containing a antibacterial zeolite were molded by the extrusion laminating method. The film layer was laminated on both sides of a polypropylene sheet of a glove body 100 μm in thickness. Then, both surfaces of the laminated sheet were embossed using emboss rolls each having a square pattern 1 mm long on each side and 0.05 to 3 mm deep formed on their respective surfaces, and were molded in the shape of a glove to provide a sterilized glove. The resultant sterilized glove therefore had embossed surfaces.

Further, a sample containing no antibacterial zeolite (comparative example 1) and a sample containing a antibacterial zeolite but undergone no embossing (comparative example 2) were produced.

The sterilized glove obtained by the fabrication example has a shape as shown in FIGS.1 and 2.

Molding a sterilized glove 1 as shown in FIG. 1 can provide an embossed surface 2 containing a antibacterial zeolite 4 on a glove surface 3 as shown in cross section in FIG. 2.

PRACTICAL BACTERIA TEST EXAMPLE

After using the sterilized glove obtained by the fabrication example and comparative examples at home for one month, bacteria (staphylococcus, coliform bacillus) existing on the surfaces of each glove were measured using a plate method. The results are shown in Table 2.

This invention may be practiced or embodied in still other ways without departing from the spirit or essential characteristic thereof. The preferred embodiment descried in the foregoing description is therefore illustrative and not restrictive, and the scope of the invention is indicated by the appended claims and all variations which come within the meaning of the claims are intended to be embraced therein.

TABLE 1

| Sample No. | Zeolite Type | Amount Contained in Zeolite (%) | | | | Yield (g) | Composition in Mixed Solution (M/l) | | | | Solution pH | Ion Exchange (hr) |
|---|---|---|---|---|---|---|---|---|---|---|---|---|
| | | $NH_4$ | Ag | Cu | Zn | | $NH_4NO_3$ | $AgNO_3$ | $Cu(NO_3)_2$ | $Zn(NO_3)_2$ | | |
| 1 | A | 2.5 | 3.0 | — | 13.7 | 960 | 1.8 | 0.10 | — | 2.2 | 6.0 | 24 |
| 2 | A | — | 11.6 | — | — | 930 | — | 0.30 | — | — | 6.1 | 24 |
| 3 | Y | 2.8 | 5.1 | — | — | 940 | 1.8 | 0.14 | — | — | 5.7 | 24 |
| 4 | Y | 4.2 | 2.6 | 10.9 | — | 960 | 2.1 | 0.10 | 2.5 | — | 5.9 | 24 |

TABLE 2

| Experiment No. | Antibacterial Zeolite No. | Embossing Yes/No | Number of Bacteria on Cooking Board (no./cm²) | |
|---|---|---|---|---|
| | | | Staphylococcus | Coliform Bacillus |
| Exmple 1 | 1 | Yes | 0 | 0 |
| Exmple 2 | 2 | Yes | 2 | 0 |
| Exmple 3 | 3 | Yes | 0 | 0 |
| Exmple 4 | 4 | Yes | 0 | 0 |
| Comparative Example 1 | — | Yes | $3 \times 10^2$ | $6 \times 10^3$ |
| Comparative Example 2 | 1 | No | 0 | $4 \times 10$ |

What is claimed is:

1. A sterilized glove comprising:
   a glove body, and an organic polymer film layer containing an antibacterial zeolite and formed on the entirety of at least one surface of said glove body in an upheaval shape.

2. A sterilized glove according to claim 1, wherein said organic polymer film layer is approximately 3 μm thick or more.

3. A sterilized glove according to claim 1, wherein said organic polymer film layer is formed on both surfaces of said glove body.

4. A sterilized glove according to claim 1, wherein said organic polymer film layer has a surface area approximately 120 % or more of that of said glove body.

5. A sterilized glove according to claim 1, wherein said upheaval shape is approximately 0.02 to 0.2 mm high in a direction of thickness of said organic polymer film layer.

6. A sterilized glove according to claim 1, wherein said organic polymer film layer mainly consists of polyethylene.

* * * * *